United States Patent
Nagasaka

(10) Patent No.: US 9,980,842 B2
(45) Date of Patent: May 29, 2018

(54) MOTION ASSIST DEVICE AND MOTION ASSIST METHOD, COMPUTER PROGRAM, AND PROGRAM RECORDING MEDIUM

(75) Inventor: Kenichiro Nagasaka, Tokyo (JP)

(73) Assignee: SONY CORPORATION, Tokyo (JP)

( * ) Notice: Subject to any disclaimer, the term of this patent is extended or adjusted under 35 U.S.C. 154(b) by 276 days.

(21) Appl. No.: 14/241,340

(22) PCT Filed: Jul. 3, 2012

(86) PCT No.: PCT/JP2012/066956
§ 371 (c)(1),
(2), (4) Date: Feb. 26, 2014

(87) PCT Pub. No.: WO2013/046840
PCT Pub. Date: Apr. 4, 2013

(65) Prior Publication Data
US 2014/0221894 A1 Aug. 7, 2014

(30) Foreign Application Priority Data
Sep. 26, 2011 (JP) .................................. 2011-209337

(51) Int. Cl.
*A61F 5/00* (2006.01)
*A61F 5/01* (2006.01)
(Continued)

(52) U.S. Cl.
CPC .................. *A61F 5/01* (2013.01); *A61H 3/00* (2013.01); *B25J 9/0006* (2013.01); *A61H 1/024* (2013.01);
(Continued)

(58) Field of Classification Search
CPC .... A61H 2201/165; A61H 3/00; A61H 1/024; A61H 2201/1215; A61H 2201/5007;
(Continued)

(56) References Cited

U.S. PATENT DOCUMENTS 7,190,141 B1 * 3/2007 Ashrafiuon ............ B25J 9/0006
318/568.12
7,628,766 B1 * 12/2009 Kazerooni ................ A61F 5/00
601/35

(Continued)

FOREIGN PATENT DOCUMENTS

JP 2003-220584 A 8/2003
JP 2006-293624 A 10/2006

(Continued)

OTHER PUBLICATIONS

Combined Chinese Office Action and Search Report issued Apr. 3, 2015 in Patent Application No. 201280045574.X (with English language translation).

(Continued)

*Primary Examiner* — Kim M Lewis
(74) *Attorney, Agent, or Firm* — Oblon, McClelland, Maier & Neustadt, L.L.P.

(57) ABSTRACT

Intentions of a user are read from movements of the joints of the user without the use of a myoelectric sensor, and a force to support motions of the user is generated.
Even if there is friction that is difficult to model in a gear portion of a joint actuator, the friction is compensated for, and joint units are controlled to follow an idealized mathematical model. In this manner, the force to support motions is generated, without giving any uncomfortable feeling to the joints of the user wearing the device. When motions of the user are supported, a mathematically-determined torque is applied to the joint units, so that a natural supporting force is constantly provided to the user in various circumstances.

12 Claims, 7 Drawing Sheets

(51) Int. Cl.
*A61H 3/00* (2006.01)
*B25J 9/00* (2006.01)
*A61H 1/02* (2006.01)

(52) U.S. Cl.
CPC .......... *A61H 1/0244* (2013.01); *A61H 1/0266* (2013.01); *A61H 2201/165* (2013.01); *A61H 2201/5007* (2013.01); *Y10S 901/02* (2013.01)

(58) Field of Classification Search
CPC .... A61H 2201/5061; A61H 2201/5069; A61H 1/0244; A61H 1/0262; A61H 1/0266; A61H 2201/14; A61H 2201/1463; A61H 3/008; A61H 2201/149; A61H 2201/1623; A61H 2201/1633; A61H 2201/1642; A61H 2201/1676; A61H 1/0237; A61H 1/0255; A61F 5/00; A61F 2/68; A61F 2/6607; A61F 2002/7635; A61F 2002/704; A61F 2002/7625; A61F 2002/701; A61F 2002/7645; A61F 2002/764; A61F 2/72; A61F 2002/5018; A61F 2/60; A61F 2/64; A61F 2002/503; A61F 5/01; B25J 9/0006; B25J 13/085; B25J 9/1633; Y10T 29/49826; Y10T 4/20317; A61B 5/4528; A61B 5/112; A61B 5/1038; A61B 2562/0247; A61B 2562/046; A61B 5/1036; A61B 5/1071; A61B 5/4851; A61B 5/1123; A61B 5/6828; A61B 5/6807; A61B 2560/0462; A61B 2562/0219; Y10S 901/02; G06K 9/00348; G05B 2219/39319
USPC ........ 602/13, 23, 26–28, 16; 601/23, 27, 29, 601/31–35; 623/47–52; 901/1, 2, 9, 15, 901/27, 28, 46, 47; 700/245, 260, 261, 700/30, 254
See application file for complete search history.

(56) References Cited

U.S. PATENT DOCUMENTS

| | | | | | |
|---|---|---|---|---|---|
| 2004/0254679 | A1* | 12/2004 | Nagasaka | ............ | B62D 57/032 700/245 |
| 2005/0107916 | A1* | 5/2005 | Nagasaka | ............ | B62D 57/032 700/245 |
| 2009/0036815 | A1* | 2/2009 | Ido | ....................... | A61H 1/0237 602/23 |
| 2009/0272585 | A1* | 11/2009 | Nagasaka | .............. | B25J 9/1633 180/8.6 |
| 2010/0145239 | A1* | 6/2010 | Kudoh | .................... | A61H 3/008 601/34 |
| 2010/0152630 | A1* | 6/2010 | Matsuoka | .............. | A61H 3/008 601/35 |
| 2010/0204627 | A1* | 8/2010 | Kazerooni | ................ | A61F 5/00 602/16 |
| 2010/0206651 | A1* | 8/2010 | Nagasaka | ................ | B25J 5/007 180/218 |
| 2010/0234777 | A1* | 9/2010 | Yasuhara | ............... | B25J 9/0006 601/35 |

FOREIGN PATENT DOCUMENTS

| | | |
|---|---|---|
| JP | 2007-533375 | 11/2007 |
| JP | 2009-269102 A | 11/2009 |
| JP | 2010-142351 A | 7/2010 |
| JP | 2010-179442 A | 8/2010 |
| JP | 2011-62463 A | 3/2011 |
| JP | 4715863 | 4/2011 |
| WO | WO 2010/032493 A1 | 3/2010 |

OTHER PUBLICATIONS

Office Action issued Sep. 29, 2015 in Japanese Patent Application No. 2011-209337.
Extended European Search Report issued Jul. 16, 2015 in Patent Application No. 12837119.2.
International Search Report issued Oct. 9, 2012 in PCT/JP2012/066956.
Kenta Suzuki, et al., "Intention-based walking support for paraplegia patients with Robot Suit HAL", Advanced Robotics, vol. 21, No. 12, 2007, pp. 1441-1469.
Hiroaki Kawamoto, et al., "Power assist method for HAL-3 using EMG-based feedback controller", IEEE, 2003, pp. 1648-1653.
Justin Ghan, et al., "Control and system identification for the Berkeley lower extremity exoskeleton (BLEEX)", Advanced Robotics, vol. 20, No. 9, 2006, pp. 989-1014.
Office Action issued Apr. 26, 2016 in Japanese Patent Application No. 2011-209337 (with English language translation).
Office Action dated Jun. 3, 2017, in Japanese Patent Application No. 2016-146984.

* cited by examiner

MOTION ASSIST DEVICE AND MOTION ASSIST METHOD, COMPUTER PROGRAM, AND PROGRAM RECORDING MEDIUM

TECHNICAL FIELD

The technique disclosed in this specification relates to a motion assist device that is attached to the body of a person such as an elderly person who needs assistance or nursing care, and physically and mentally assists motions of the body of the person. The technique also relates to a motion assist method, a computer program, and a program recording medium. More particularly, the technique relates to a motion assist device that assists various kinds of general motions of the human body such as a walking motion. The technique also relates to a motion assist method, a computer program, and a program recording medium.

BACKGROUND ART

The proportion of the elderly in our country (the ratio of people aged 65 or over to total population) was 23.1% in 2010, and is predicted to become as high as 30% in 2025. As the proportion of the elderly in the demographic structure is rapidly increasing, it is urgent to realize a society in which the elderly can live as actively and as healthily as possible without requiring any nursing care, and, even if in need of care, they can live as independently as possible while preventing symptoms from worsening.

In response to the arrival of the aging society, there is an increasing demand for mechanical and electronic devices for physically and mentally supporting the elderly in nursing facilities and households with elderly family members. Also, there are demands not only for physical assistance such as walking aid devices or power assist suits, but also for mental assistance that effectively incorporates robots into work therapies.

One of the important points in the development of mechanical and electronic devices for assistance and care is not to unnecessarily interfere with activities of the elderly but to maintain and facilitate such activities. If a machine carries out activities for an elderly person just because the physical strength of the elderly person has weakened, his/her physical strength will deteriorate further, and the situation worsens (disuse syndrome). A power assist suit is a device that generates an artificial force to reinforce power generated by the muscles of a person. This is a desirable device in keeping an elderly person continuing his/her activities while supplementing the weakening physical strength of the elderly person.

However, the penetration rate of power assist suits is not high at present. The possible reasons for that are as follows.
(1) Wearing it is troublesome.
(2) Only clumsy supports are provided.
(3) It looks bad when worn.
(4) The machine is heavy in weight.
(5) The operating time is short.

For example, attention is recently drawn to a power assist method for giving a drive force to joints based on outputs from myoelectric sensors and results of motion phase estimation (see Non-Patent Document 1, for example). However, as many as nine myoelectric sensors need to be attached to each arm, and it is troublesome to attach those sensors. Also, myoelectric sensors might come off the skin due to deterioration with time or sweat. When the adhesion between a myoelectric sensor and the skin weakens, the output value of the myoelectric sensor becomes unstable. As a result, the power assist suit might run out of control, or an inappropriate force might be applied to the body of the person wearing the power assist suit.

There is also a suggestion for a walking assist device that applies a torque pattern designed in accordance with phases of walking to the body of a person when the person is walking (see Non-Patent Document 2, for example). There are various walking patterns in one user, and the designed torque pattern is often unable to cope with the various patterns. As a result, the user feel uncomfortable while walking, or can walk only in an unnatural manner at a low speed.

Meanwhile, there is a suggestion for a body assist device that does not involve myoelectric sensors (see Non-Patent Document 3, for example). This device senses motions of the joints of the user, and applies supporting forces to the joints. However, if there is hindrance to motions of the joints of the user, it is difficult for this device to reflect intentions of the user at a high sensitivity. For example, the viscous resistance of the gear portions included in the joint units of a conventional power assist suit might cause hindrance to motions of the joints of the user. It is considered that that such impediments need to be eliminated in the future.

Also, forces generated by a power assist suit are often based on an experimental rule or an invalid control law. Ideally, myoelectric sensors can directly reflect a user's intention to move (in reality, however, it is difficult for myoelectric sensors to sense motions in a preferred manner, as described above). On the other hand, it is difficult to read a user's intention from sensed motions of joints. Under such circumstances, it is considered that a valid control law is required so as to provide supporting forces to users without stress and artificiality.

For example, there is a suggestion for a walking assist system that assists walking movements of legs while keeping the user's body balance and supporting the user's body weight (see Patent Document 1, for example). This walking assist system is formed with an inverted-pendulum mobile unit to be held by the user and a walking aid device that assists movements of the legs of the user. A predetermined velocity relationship is to be established between the inverted-pendulum mobile unit and the walking aid device in terms of target moving velocity. The inverted-pendulum mobile unit controls moves based on motions of the base and the target moving velocity when held by the user, and the walking aid device transfers forces to the user based on the motions of the legs of the user and the target moving velocity. However, the walking assist system assists only walking motions, and does not have the versatility to cope with other types of motions of the human body.

CITATION LIST

Patent Document

Patent Document 1: Japanese Patent Application Laid-Open No. 2011-62463

Non-Patent Documents

Non-Patent Document 1: Kawamoto H., Lee S., Kanbe S., Sankai Y.: "Power Assist Method for HAL-3 using EMG-based Feedback Controller", Proc. of Int'l Conf. onSystems, Man and Cybernetics (SMC2003), pp. 1648-1653, 2003

Non-Patent Document 2: Kenta Suzuki, Gouji Mito, Hiroaki Kawamoto, Yasuhisa Hasegawa, Yoshiyuki Sankai:

"Intention-Based Walking Support for Paraplegia Patients with Robot Suit HAL", Advanced Robotics, Vol. 21, No. 12, pp. 1441-1469, 2007

Non-Patent Document 3: J. Ghan, R. Steger, Kazerooni, H, "Control and System Identification for the Berkeley Lower Extremity Exoskeleton", Advanced Robotics, Volume 20, Number 9, pp. 989-1014, Number 9, 2006

SUMMARY OF THE INVENTION

Problems to be Solved by the Invention

An object of the technique disclosed in this specification is to provide an excellent motion assist device that is attached to the body of a person such as an elderly person who needs assistance or nursing care, and can physically and mentally assist motions of the person's body in a suitable manner, and is also to provide a motion assist method, a computer program, and a program recording medium.

Another object of the technique disclosed in this specification is to provide an excellent motion assist device that can read intentions of a user from motions of the joints of the user without the use of a myoelectric sensor, generate a supporting force to the user without stress and artificiality, and assist various kinds of general motions of the human body, and is also to provide a motion assist method, a computer program, and a program recording medium.

Solutions to Problems

This application has been made in view of the above problems, and the technique disclosed in claim 1 is a motion assist device that includes:

a link structure formed with joint units and links that connect the joint units;

an actuator that actuates the joint units through torque control;

a joint value measuring unit that measures a joint value of the joint units;

a target torque determining unit that determines a target torque for the actuator based on the joint value measured by the joint value measuring unit;

a torque measuring unit measures an external torque acting on the joint units; and a response control unit performs torque control on the actuator, to establish a desired relationship among the target torque, the joint value measured by the joint value measuring unit, and the external torque measured by the torque measuring unit.

According to the technique disclosed in claim 2 of this application, the target torque determining unit of the motion assist device of claim 1 is designed to determine the target torque to reduce the load on the joints of a human body having the link structure attached thereto.

According to the technique disclosed in claim 3 of this application, the target torque determining unit of the motion assist device of claim 1 is designed to determine the target torque to make the accelerations of the joint units zero.

According to the technique disclosed in claim 4 of this application, the motion assist device of claim 1 further includes a posture measuring unit that measures the tilt of part of the link structure. The target torque determining unit is designed to determine the target torque by using a dynamics model of the link structure and a human body having the link structure attached thereto, the dynamics model reflecting the tilt measured by the posture measuring unit and the joint value measured by the joint value measuring unit.

According to the technique disclosed in claim 5 of this application, the target torque determining unit of the motion assist device of claim 4 is designed to determine the target torque to cancel or reduce the load on the joints of the human body having the link structure attached thereto.

According to the technique disclosed in claim 6 of this application, the motion assist device of claim 5 further includes a contact measuring unit that measures the contact state at a contact site where the link structure is assumed to be in contact with the outside. The target torque determining unit is designed to determine the target torque based on the contact state at the contact site measured by the contact measuring unit.

According to the technique disclosed in claim 7 of this application, the target torque determining unit of the motion assist device of claim 6 is designed to determine the target torque by using quadratic programming, the target torque satisfying a purpose of motion of the link structure and a constraint condition imposed on the link structure.

According to the technique disclosed in claim 8 of this application, the response control unit of the motion assist device of claim 1 is designed to perform the torque control on the actuator, to cause the joint units to make an ideal quadratic response to the target torque and the external torque measured by the torque measuring unit.

According to the technique disclosed in claim 9 of this application, the response control unit of the motion assist device of claim 1 includes a disturbance observer that calculates a disturbance torque $\tau_d$ when the actuator is actuated with the target torque $\tau_A$, and the response control unit is designed to correct a torque target value $\tau^{ref}$ with the disturbance torque $\tau_d$ obtained by the disturbance observer in the previous control cycle, to determine a command torque $\tau_e$ for the actuator in the current control cycle, the torque target value $\tau^{ref}$ being obtained by multiplying a joint value acceleration target value by the nominal value $J_n$ of inertia in the joint units, the joint value acceleration target value being obtained from a theoretical response model that is output by determining the joint value acceleration target value to be achieved when the actuator responds based on the target torque $\tau_A$, the external torque $\tau_e$, and a joint value velocity obtained by temporally differentiating the joint value q.

The technique disclosed in claim 10 of this application is a motion assist method that includes:

a joint value measuring step of measuring a joint value of a joint unit in a link structure formed with joint units and links that connect the joint units;

a target torque determining step of determining a target torque for an actuator based on the joint value measured in the joint value measuring step, the actuator actuating the joint units;

a torque measuring step of measuring an external torque acting on the joint units; and a response control step of performing torque control on the actuator, to establish a desired relationship among the target torque, the joint value measured in the joint value measuring step, and the external torque measured in the torque measuring step.

The technique disclosed in claim 11 of this application is a computer program written in a computer-readable format to cause a computer to carry out:

a joint value acquiring step of acquiring a joint value of a joint unit in a link structure formed with joint units and links that connect the joint units;

a target torque determining step of determining a target torque for an actuator based on the joint value measured in the joint value measuring step, the actuator actuating the joint units;

a torque acquiring step of acquiring an external torque acting on the joint units; and a response control step of performing torque control on the actuator, to establish a desired relationship among the target torque, the joint value acquired in the joint value measuring step, and the external torque measured in the torque acquiring step.

The computer program according to claim 11 of this application defines a computer program that is written in a computer-readable format to realize predetermined processing in a computer. In other words, the computer program according to claim 11 of this application is installed into a computer, so that cooperative actions are realized in the computer, and the same effects as those of the motion assist device according to claim 1 of this application can be achieved.

The technique disclosed in claim 12 of this application is a program recording medium storing a computer program written in a computer-readable format to cause a computer to carry out:

a joint value acquiring step of acquiring a joint value of a joint unit in a link structure formed with joint units and links that connect the joint units;

a target torque determining step of determining a target torque for an actuator based on the joint value measured in the joint value measuring step, the actuator actuating the joint units;

a torque acquiring step of acquiring an external torque acting on the joint units; and a response control step of performing torque control on the actuator, to establish a desired relationship among the target torque, the joint value acquired in the joint value measuring step, and the external torque measured in the torque acquiring step.

Effects of the Invention

According to the technique disclosed in this specification, it is possible to provide an excellent motion assist device that is attached to the body of a person such as an elderly person who needs assistance or nursing care, and can physically and mentally assist motions of the person's body in a preferred manner. It is also possible to provide a motion assist method, a computer program, and a program recording medium.

According to the technique disclosed in this specification, it is possible to provide an excellent motion assist device that is easy to wear, senses intentions of the user in a stable manner, excels in sensitivity and readiness, and can provide natural supporting forces without causing the user to feel stress. It is also provide a motion assist method, a computer program, and a program recording medium.

The technique disclosed in this specification is a motion assist device that reads intentions of a user from movements of the joints of the user without the use of a myoelectric sensor, and generates a force to support motions of the user. Even if there is friction that is difficult to model in a gear portion of a joint actuator, the friction is compensated for, and joint units are controlled to follow an idealized mathematical model. In this manner, the force to support motions can be generated, without giving any uncomfortable feeling to the joints of the user wearing the device. When motions of the user are supported, a mathematically-determined torque is applied to the joint units, so that a natural supporting force can be constantly provided to the user in various circumstances. Specifically, a state where no forces are applied to the joints of the user (as if in space) is approximated as much as possible.

Other objects, features, and advantages of the technique disclosed in this specification will become more apparent from the following detailed description of embodiments in conjunction with the accompanying drawings.

MODES FOR CARRYING OUT THE INVENTION

The following is a detailed description of embodiments of the present invention, with reference to the drawings.

Figure 1:
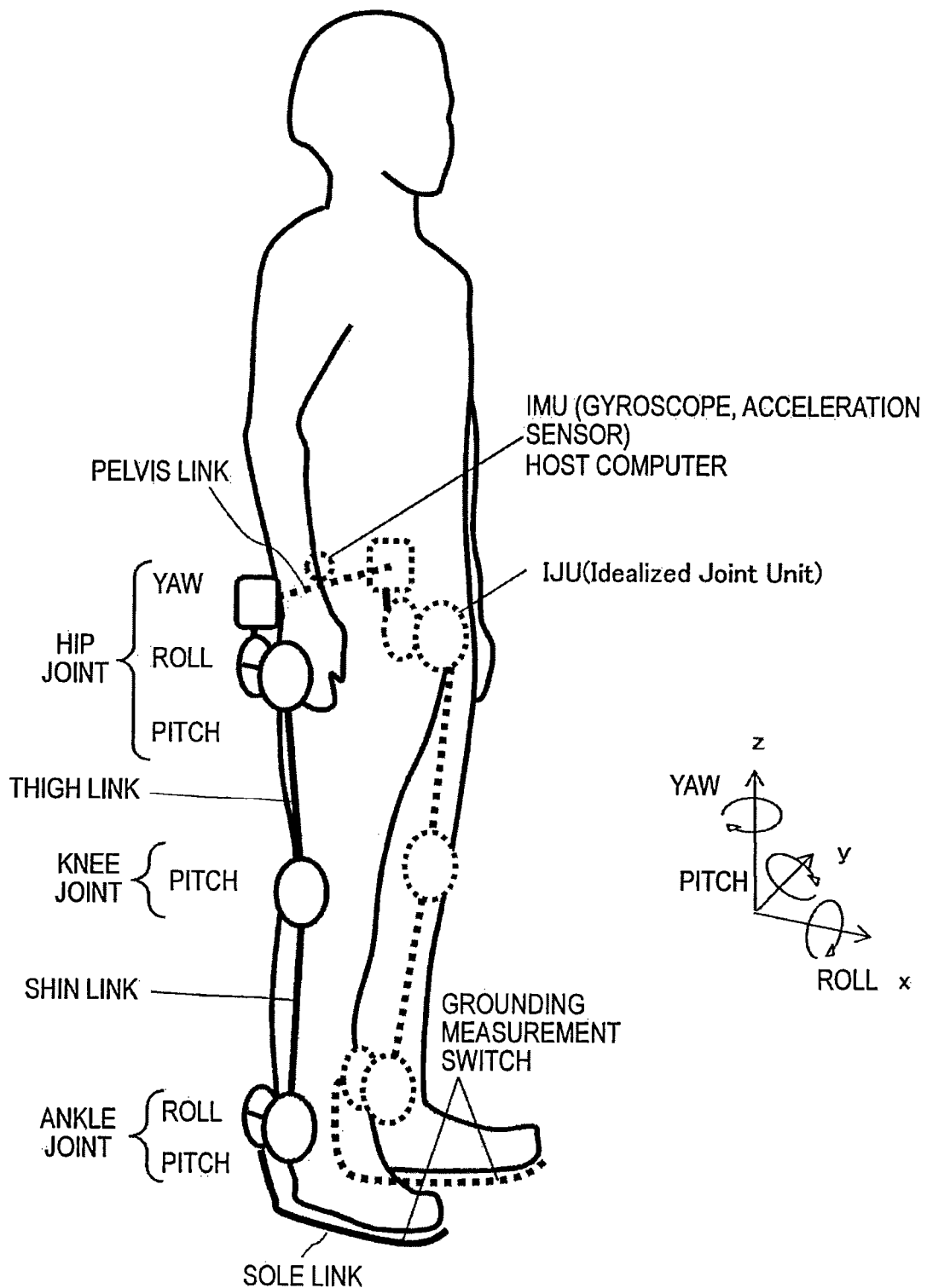
FIG. 1 is a diagram schematically showing the structure of a leg assist suit to which the technique disclosed in this specification is applied.

FIG. 1 schematically shows the structure of a leg assist suit to which the technique disclosed in this specification is applied.

For each of the right and left legs of a human body, the leg assist suit shown in the drawing has a total of 12 freedom degrees including the three freedom degrees of roll, pitch, and yaw at the hip joint, the one freedom degree of pitch at the knee joint, and two freedom degrees of roll and pitch at the ankle. The joint axis at each joint unit is actuated by an actuator for actuating a joint.

The respective joints are connected by rigid links. Specifically, the right and left hip joints are connected by a pelvis link, the hip joint and the knee joint of each of the right and left legs are connected by a thigh link, and the knee joint and the ankle joint of each of the right and left legs are connected by a shin link. A sole link is connected to each of the ankle joints. Each of the pelvis link, the thigh links, the shin links, and the sole links is fixed to the human body by a band (not shown).

In FIG. 1, the joint units and the links of the right side are drawn with solid lines, and the joint units and the links of the left side that are hidden by the human body are drawn with dotted lines.

A host computer that performs central control is mounted on the pelvic region. The above mentioned actuators for actuating the joint axes of the respective joint units each include a microcomputer (not shown) that can communicate with the host computer. Control target values of the joints are given to the respective microcomputers from the host computer, and detected joint angles and joint angular velocities are transmitted from the respective microcomputers to the host computer.

A contact sensor for detecting a contact state between the sole of the foot and the road surface is mounted on each of the right and left sole regions. As the contact sensor, a grounding measurement switch that is on when the sole of the foot is in contact with the road surface, and is off when the sole of the foot is not in contact with the road surface is used. A microcomputer accompanying the contact sensor reads ON/OFF values of the contact sensor, and transmits the ON/OFF values to the host computer.

An IMU formed with a triaxial acceleration sensor and a triaxial angular velocity sensor (a gyroscope) is mounted on the pelvic region. A microcomputer that measures values of those sensors is provided near the pelvic region, and measurement results are transmitted from the microcomputer to the host computer.

Figure 2:
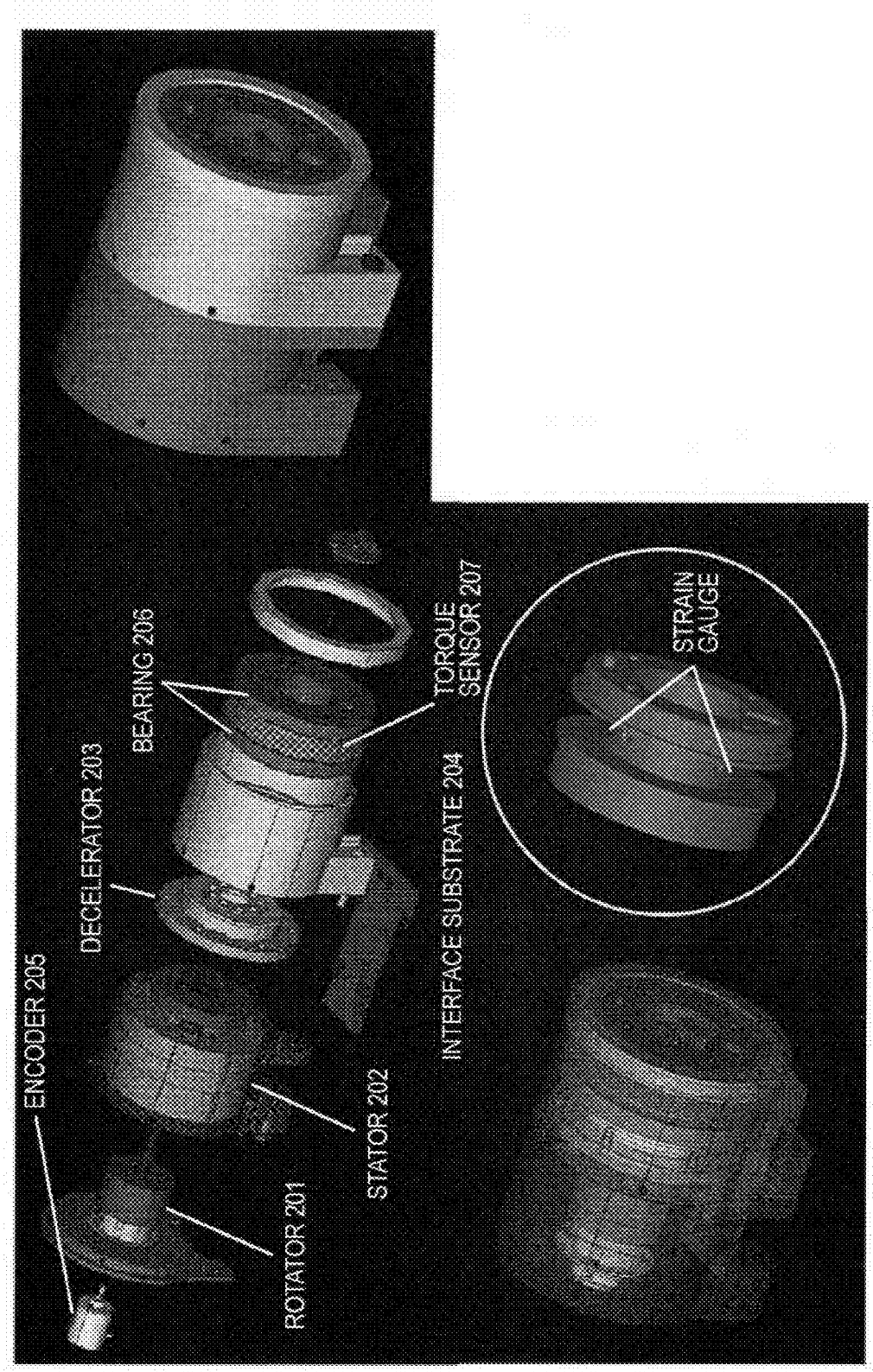
FIG. 2 is a diagram showing the structure of an actuator device used for each of the joints of the leg assist suit shown in FIG. 1.

FIG. 2 shows the structure of an actuator device used for each of the joints of the leg assist suit shown in FIG. 1. The actuator device shown in the drawing includes a motor main body formed with a rotator 201 and a stator 202, and a decelerator 203 formed with a gear such as a wave gear mechanism. The actuator device is mounted on an interface substrate 204. An encoder 205 that senses a rotational position or an angle of the joint axis is attached to the rotator of the motor. A later-stage link (not shown) is connected to the output axis of the decelerator via bearings 206, and a torque sensor 207 for sensing an output torque is also attached to the output axis.

For the actuator on each junction axis, an actuator control device that can cope with causes of external disturbances that are difficult to model or identify, such as frictions and joints existing in the joint units, and can designate an output torque based on a mathematical model (an idealized response model) is used, and the actuator is preferably an idealized joint unit (IJU). For example, this type of actuator device is disclosed in Japanese Patent Publication No. 4715863, which has already been assigned to the applicant. This actuator device indicates a precise quadratic response controlled by designated inertia and viscous resistance, in response to a command torque and an external torque. As a result, motions of the joints are not hindered by frictions in the gear of the decelerator, and even a small force acting on a joint can be accurately turned into a change in angular velocity of the actuator. Accordingly, a precise response based on a mathematical model can be realized by performing control using an output torque obtained through the torque sensor and angles detected by the encoder.

Figure 3:
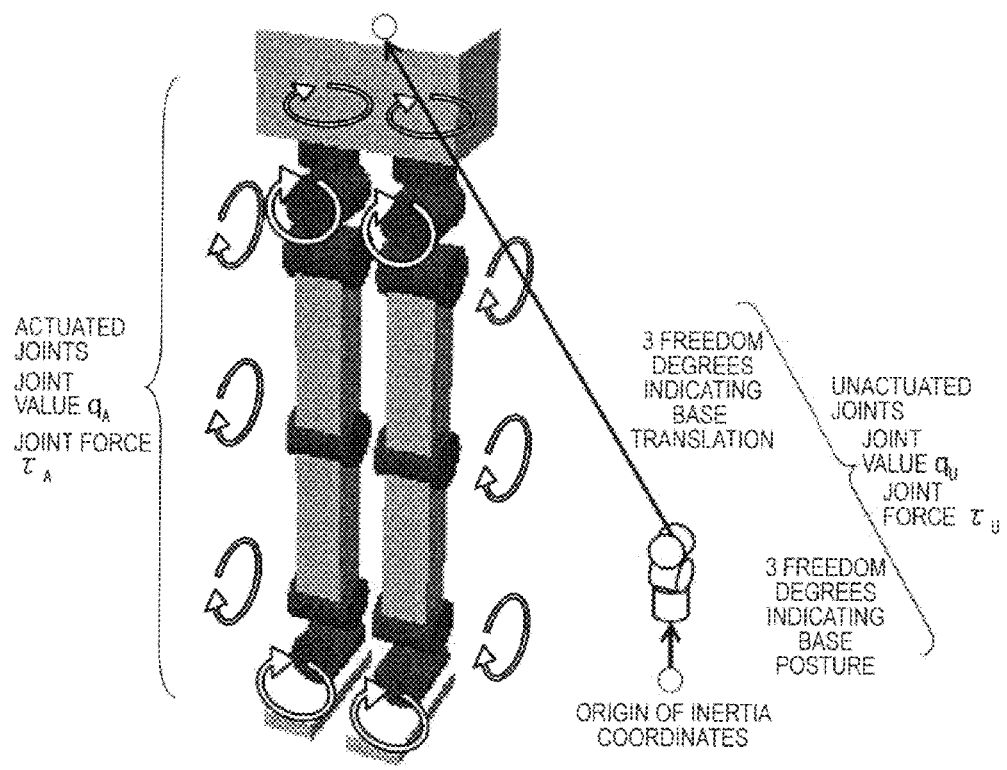
FIG. 3 is a diagram showing a two-legged robot that models after a system that combines a person and the leg assist suit shown in FIG. 1.

Here, the mass property of the person who wears the leg assist suit shown in FIG. 1 is already known, and the system formed by combining the person and the leg assist suit is modeled as a two-legged robot as shown in FIG. 3. The model in the drawing has the freedom degree components of the above described joints (the three freedom degrees of the hip joint, the one freedom degree of the knee joint, and the two freedom degrees of the ankle of each of the right and left legs), and freedom degree components indicating positions and postures of the pelvic region. The former are the freedom degrees of the actually existing (or actuated) joints. The joint value thereof is represented by $q_A$, and the joint force thereof is represented by $\tau_A$, with the meaning of "being actuated" being hidden therein. Meanwhile, the latter are formed with a total of six freedom degrees including three freedom degrees indicating base translations of the pelvic region with respect to the origin of the joint coordinate system, and three freedom degrees indicating base postures. However, any force cannot be generated. Therefore, the joint value thereof is represented by $q_U$, and the joint force thereof is represented by $\tau_U$, with the meaning of "being unactuated" being hidden therein. A torque that can be generated from each of the joint units of the leg assist suit is a torque generated by an actuator for actuating an actually existing joint. A force generated by a muscle of the person wearing the leg assist suit is regarded as an external force from the viewpoint of this system.

The leg assist suit according to this embodiment aims to enable a person who wears it to move with a very weak muscle force without feeling the weight of his/her body even when the muscle force of the person wearing the leg assist suit has weakened. In other words, creating a situation where a person moves as if in a zero-gravity environment is a purpose of motion of the leg assist suit. For example, when a person stands up from a chair or climbs up and down stairs, most of the force to support his/her body weight is generated by actuators, so that the muscles of the person generate only the small remaining amount of force required. For ease of explanation, cases where the mass property of a person changes, such as when the person lifts a heavy object onto his/her back, are excluded from the cases described below.

To achieve the above described purpose of motion, a control system that compensates for part of the load acting on the joints of a person due to gravity with actuators is formed. In the case of a two-legged robot as shown in FIG. 3, however, various grounded states such as a left-leg grounded state, a right-leg grounded state, a two-leg grounded state, and a non-grounded state are involved, and the system dynamics greatly vary depending on the grounded states. In a case where the two-legged robot is of a one-leg supported type, the two-legged robot is controlled by dynamics similar to those of a redundant manipulator. In a case where the two-legged robot is of a two-leg supported type, a closed loop is formed, and the decision rule for torque is not simple. In the case of a problem without a solution (an insoluble problem), an approximate torque needs to be generated. In the case of a problem with infinite solutions (an indeterminate problem), an optimum torque pattern that applies the lowest load to the system among the numerous solutions needs to be formed. It is preferable to remove the complexities of switching between control systems as such walking phase transitions occur. A control system that can comprehensively deal with those problems is described below.

The motion equation of a bipedal walking system can be expressed as in the following equation (1).

$$\tau = H\ddot{q} + b(\dot{q}, g) - J_E^T f_E \qquad \text{[Mathematical Formula 1]}$$

In the above equation (1), $\tau$ represents the generalized force corresponding to a generalized variable q, b represents gravity or Coriolis force, H represents the inertia matrix corresponding to the joint space of the two-legged robot (the entire link structure), $f_E$ represents external force (floor reaction force), and $J_E$ represents the Jacobian associating the space on which the external force $f_E$ acts with the joint space. The generalized variable q herein is the joint value of the two-legged robot that is modeled as in FIG. 3, and the generalized force $\tau$ is equivalent to the joint force. More specifically, the generalized variable q is formed with 12 freedom degree components of the actually existing joints (the three freedom degrees of the hip joint, the one freedom degree of the knee joint, and the two freedom degrees of the ankle of each of the right and left legs), and six freedom degree components indicating positions and postures of the pelvic region. The generalized variable of the former is represented by $q_A$, and the generalized force is represented by $\tau_A$, with the meaning of "being actuated" being hidden therein. Since the latter cannot generate a force, the generalized variable thereof is represented by $q_U$, and the generalized force thereof is represented by $\tau_U$, with the meaning of "being unactuated" being hidden therein. Accordingly, the generalized force $\tau$ and the generalized variable q can be expressed as $\tau = (\tau^T_U \tau^T_A)^T$ and $q = (q^T_U q^T_A)^T$. When the motion equation is divided into unactuated components and actuated components, the above equation (1) can be transformed into the following equation (2).

$$H\ddot{q} + b = \begin{bmatrix} \tau_U \\ \tau_A \end{bmatrix} + J^T_E f_E \quad \text{[Mathematical Formula 2]}$$

A key concept in robot control in a force control system is the space for describing the relationship between the force acting on the robot and a generated acceleration, or the operational space. For example, as the positions of the soles of the feet of the two-legged robot are defined as the operational space, the operational space is used in determining the joint force for generating a desired acceleration in the soles. Normally, a velocity of an operational space x is expressed as in the following equation (3-1) using the joint velocity and the Jacobian J of a joint q. Accordingly, the acceleration of the operational space x is expressed as in the following equation (3-2) using the joint velocity and the Jacobian of the joint q. The operational space eventually becomes equal to the joint space.

$$\dot{x} = J\dot{q}$$

$$\ddot{x} = J\ddot{q} + \dot{J}\dot{q} \quad \text{[Mathematical Formula 3]}$$

When the acceleration component of the generalized variable q is eliminated from the above equation (3-2) by using the above equation (2), the following equation (4) is obtained.

$$\ddot{x} = JH^{-1}\left\{\begin{bmatrix} \tau_U \\ \tau_A \end{bmatrix} + J^T_E f_E - b\right\} + \dot{J}\dot{q} \quad \text{[Mathematical Formula 4]}$$

Since unactuated joints cannot generate torque as described above, $\tau_U = 0$. With this being substituted into the above equation (4), the following equation (5) is obtained.

$$\ddot{x} = [JH^{-1}_A \quad JH^{-1}J^T_E]\begin{bmatrix} \tau_A \\ f_E \end{bmatrix} - JH^{-1}b + \dot{J}\dot{q} \quad \text{[Mathematical Formula 5]}$$

In the above equation (5), however, the inverse matrix $H^{-1}$ of the inertia matrix can be divided into the column $H^{-1}_A$ of the actuated joints and the column $H^{-1}_U$ of the unactuated joints, and be expressed as $H^{-1} = [H^{-1}_A H^{-1}_U]$. If the above equation (5) is further simplified, the motion equation of the bipedal walking system shown in the above equation (1) can be transformed into the following equation (6) expressing the dynamics related to the operational space x.

$$\ddot{x} = \Lambda^{-1}_H \begin{bmatrix} \tau_A \\ f_E \end{bmatrix} + c_H \quad \text{[Mathematical Formula 6]}$$

The above equation (6) expresses the relationship between the acceleration generated in the operational space x and the torque $\tau_A$ of the actuated joints and the external force $f_E$ acting on the operational space x. However, $\Lambda^{-1}_H$ and $c_H$ in the above equation (6) are expressed as in the following equations (7) and (8), respectively.

$$\Lambda^{-1}_H = [JH^{-1}_A JH^{-1}J^T_E] \quad \text{[Mathematical Formula 7]}$$

$$c_H = -JH^{-1}b + \dot{J}\dot{q} \quad \text{[Mathematical Formula 8]}$$

The acceleration of the operational space x shown in the left-hand side of the above equation (6) can be regarded as a purpose of motion of the leg assist suit. Examples of motion purposes include setting the acceleration of a particular portion of the object being controlled at 0, setting the velocity at 0, and setting a value given with a position (as will be described later, a motion purpose to set the joint acceleration at 0 is set in the leg assist suit so that a support force for maintaining the passive and current motion at the joints will be generated). As will be described later, $\Lambda^{-1}_H$ and $c_H$ appearing in the right-hand side are known quantities that can be calculated in accordance with the state of the system. By determining the unknown quantities $\tau_A$ and $f_E$ with respect to those known quantities, it is possible to obtain the values of the actuated joint force $\tau_A$ for achieving a motion purpose and the external force $f_E$ that the system should obtain from the space expressed by the Jacobian $J_E$.

However, the actuated joint force $\tau_A$ has a limit, and external forces obtained from outside are constrained by a cone of friction or a supporting polygon. Also, a solution that satisfies the above equation (6) does not necessarily always exist. In case there are no solutions that satisfy any motion purpose, a mechanism to prioritize motion purposes becomes necessary. On the contrary, there are cases where numerous solutions exist, and an appropriate solution needs to be selected. Therefore, solving the above equation (6) simply as a system of linear equations is insufficient.

Therefore, the above problem of determining the unknown quantity $\tau_A$ and the unknown force formed with $f_E$ is solved as a quadratic programming problem as shown in the following expressions (9) and (10), to determine an unknown force y.

$$\min \frac{1}{2} e^T W e + \frac{1}{2} y^T E y \quad \text{[Mathematical Formula 9]}$$

$$s.t.\ Ay \geq d \quad \text{[Mathematical Formula 10]}$$

In the above expressions, the unknown force y is a variable formed with the actuated joint force $\tau_A$ and the external force $f_E$, and is expressed as in the equation (11) shown below. Also, e is the value obtained by subtracting the left-hand side from the right-hand side of the above equation (6), and represents an error of the above equation (6), as in the equation (12) shown below. Satisfying the above equation (6) can be made easier by making e smaller. Also, W is a diagonal matrix defining the weight relationship among the motion purposes, and is expressed as in the equation (13) shown below. In accordance with W, a motion purpose with a greater weight can be preferentially achieved, compared with a motion purpose with a smaller weight.

$$y = \begin{bmatrix} \tau_A \\ f_E \end{bmatrix} \quad \text{[Mathematical Formula 11]}$$

$$e = \Lambda_H^{-1} y + c_H - \ddot{x} \quad \text{[Mathematical Formula 12]}$$

$$W = \text{diag}\{w_i\} \quad \text{[Mathematical Formula 13]}$$

Further, E is a diagonal matrix for causing the unknown force y to converge with the smallest solution when there are numerous solutions, and is expressed as in the equation (14) shown below. However, $\varepsilon_i$ in the equation is a sufficiently small value so as not to affect the precision of the solution.

$$E = \text{diag}\{\varepsilon_i\} \quad \text{[Mathematical Formula 14]}$$

The above expression (10) shows a constraint condition for the unknown force y. In the case of the leg assist suit, the constraint condition is for the joint force $\tau_A$ generated by the actuators and the floor reaction force $f_E$ (the floor reaction force is unidirectional). A and d represent a coefficient matrix and a constant vector, respectively, for expressing the inequality constraint (the above expression (10)) imposed on the unknown joint force $\tau_A$ and the unknown external force $f_E$. For example, when the joint force $\tau_A$ is to be limited, the following expression (15) should be expressed with A and d.

$$\min(\tau_{A_i}) = \tau_{A_i} \leq \max(\tau_{A_i}) \quad \text{[Mathematical Formula 15]}$$

Alternatively, when the external force $f_E$ acting on a contact point, or a force $(F_x, F_y, F_z)$ and a moment $(M_x, M_y, M_z)$ are to be constrained by unipolar contact, a cone of friction, and a supporting polygon, the expression (16) shown below should be expressed with A and d. Here, $\mu_t$ and $\mu_r$ represent friction coefficients, and $L_x$ and $L_y$ represent the lengths of the sides of a rectangular supporting polygon.

$$|F_x| \leq \mu_t F_z, |F_y| \leq \mu_t F_z, F_z \geq 0$$

$$|M_x| \leq L_y F_z, |M_y| \leq L_x F_z, |M_z| \leq \mu_r F_z \quad \text{[Mathematical Formula 16]}$$

To solve the quadratic programming problem expressed in the above expressions (9) and (10), $\Lambda_H^{-1}$ and $c_H$ need to be calculated in accordance with the state of the system.

A method of determining $\Lambda_H^{-1}$ and $c_H$ with a smaller amount of calculation is described below. The calculation to obtain the left-hand side from the right-hand side in the above equation (6) can be regarded as a problem of determining the acceleration in the operational space x when the joint force $\tau_A$ and the external force $f_E$ act on the system. This can be considered a kind of forward dynamics operation, though differing from a conventional forward dynamics calculation in determining the acceleration in the operational space x. The forward dynamics operation $FD_H$ has parameters such as a joint space q as a dynamics model of a link structure, the joint velocity thereof, the gravity g, and the unknown force y, and can be expressed as in the following equation (17).

$$\ddot{x} = FD_H(q, \dot{q}, g, y) \quad \text{[Mathematical Formula 17]}$$

According to this forward dynamics operation $FD_H$, the accelerations generated at respective points of the link structure can be obtained from the information about the forces acting on the link structure, such as the joint space q, the gravity g, and the unknown force y.

In the above equation (17), it is possible to determine the acceleration generated in the operational space x when forces (such as a Coriolis force) related to gravity, joint forces, and velocity products are not generated under the constraint condition that all the input parameters of the forward dynamics operation $FD_H$ other than the joint space q and the unknown force y are set at zero. That is, $c_H$ in the equation (8) can be 0. Furthermore, when a calculation according to the above equation (17) is performed under the condition that $y = u_i$ or the ith component activates a unit vector $u_i$ only in the ith operational space, the ith column of $\Lambda_H^{-1}$ can be determined. Accordingly, the entire inverse inertia matrix $\Lambda_H^{-1}$ of the operational space can be obtained by performing the forward dynamics operation shown in the following equation (18) on all the rows i.

$$\Lambda_H^{-1} \text{の 第 } i \text{ 列} = FD_H(q, 0, 0, u_i) \quad \text{[Mathematical Formula 18]}$$

First Column of $\Lambda_H^{-1}$

Also, $c_H$ can be calculated as shown in the following equation (19) by performing the forward dynamics operation $FD_H$ shown in the above equation (18) under the constraint condition that the unknown force y is 0, and only the velocity generated in the joint space q and the gravity g are active among the input parameters of the forward dynamics operation $FD_H$.

$$c_H = FD_H(q, \dot{q}, g, 0) \quad \text{[Mathematical Formula 19]}$$

A forward dynamics operation is normally formed by using an inverse dynamics operation (an operation to calculate force from acceleration) at first, but has the problem of involving a calculation amount of $O(N^3)$. As a result, the amount of operation increases as the number of freedom degrees becomes larger. On the other hand, Japanese Laid-Open Patent Publication No. 2007-108955 (described above) and R. Featherstone in "Robot Dynamics Algorithms (Kluwer Academic Publishers, 1987)" disclose a method of forming a forward dynamics operation with the calculation complexity of $O(N)$ by using the articulated body method (hereinafter referred to as the "AB method"). The AB method is disclosed in "The calculation of robot dynamics using articulated-body inertias" (Int. J. Robotics Research, vol. 2, no. 1, pp. 13-30, 1983), for example. According to the forward dynamics operation forming method disclosed in Japanese Patent Application Laid-Open No. 2007-108955, the AB method is divided into the four processes of an inertia information calculation, a velocity information calculation, a force information calculation, and an acceleration information calculation.

If the above forward dynamics operational expression (17) can be realized with the calculation complexity of $O(N)$ as with the AB method, $\Lambda_H^{-1}$ and $c_H$ can also be calculated with the same calculation complexity according to the above equations (18) and (19).

In the above manner, the quadratic programming problem expressed by the above expressions (9) and (10) can be solved. The motion purposes can be achieved by giving the joint force $\tau_A$ obtained as a solution as torque command value for the actuator to the leg assist suit.

Next, more specific settings in controlling the leg assist suit shown in FIG. 1 by using the above described control system are described.

A motion purpose of the leg assist suit is to prevent the body weight from acting on the joint units while making motions of the joint units maximally reflect the person's intentions, or to cancel or reduce the load on the joint units of the human body wearing the leg assist suit. Basically, a motion purpose is set to make the joint acceleration zero with respect to all the joints $\{q_i\}$ as shown in the following equation (20), so that a supporting force for maintaining the passive and current motion at the joints can be generated.

$$\ddot{q}_i = 0 \quad \text{[Mathematical Formula 20]}$$

The points of application of an external force in the two-legged robot model shown in FIG. 3 are assumed to be the soles of the right and left feet. At a grounding point, the soles of the feet should be supported steadily on the road surface. Therefore, the motion purposes shown in the following equations (21) and (22) related to translational acceleration and angular acceleration are set on the feet in contact with the ground.

$$a_{F_i} = 0 \quad \text{[Mathematical Formula 21]}$$

$$\dot{\omega}_{F_i} = 0 \quad \text{[Mathematical Formula 22]}$$

As for the inequality constraints, the joint force limit shown in the above expression (15) is imposed on all the joints, and the constraint shown in the above expression (16) is imposed on all the contact points.

In the above structure, torque is determined so as to maintain not only the body weight due to gravity but also inertia, and as a result, the assisting force tends to become hyperreactive. Therefore, as a state of the system, 0 is assigned to the translational velocity, the rotational velocity, and the joint angular velocity of the base on a practical level. In such a structure, the position of the entire system in world space does not affect solutions. Therefore, the position of the base portion is always set at 0 ($q_U = 0$), and the base portion reflects only the posture of the base measured by an inertia sensor.

Figure 4:
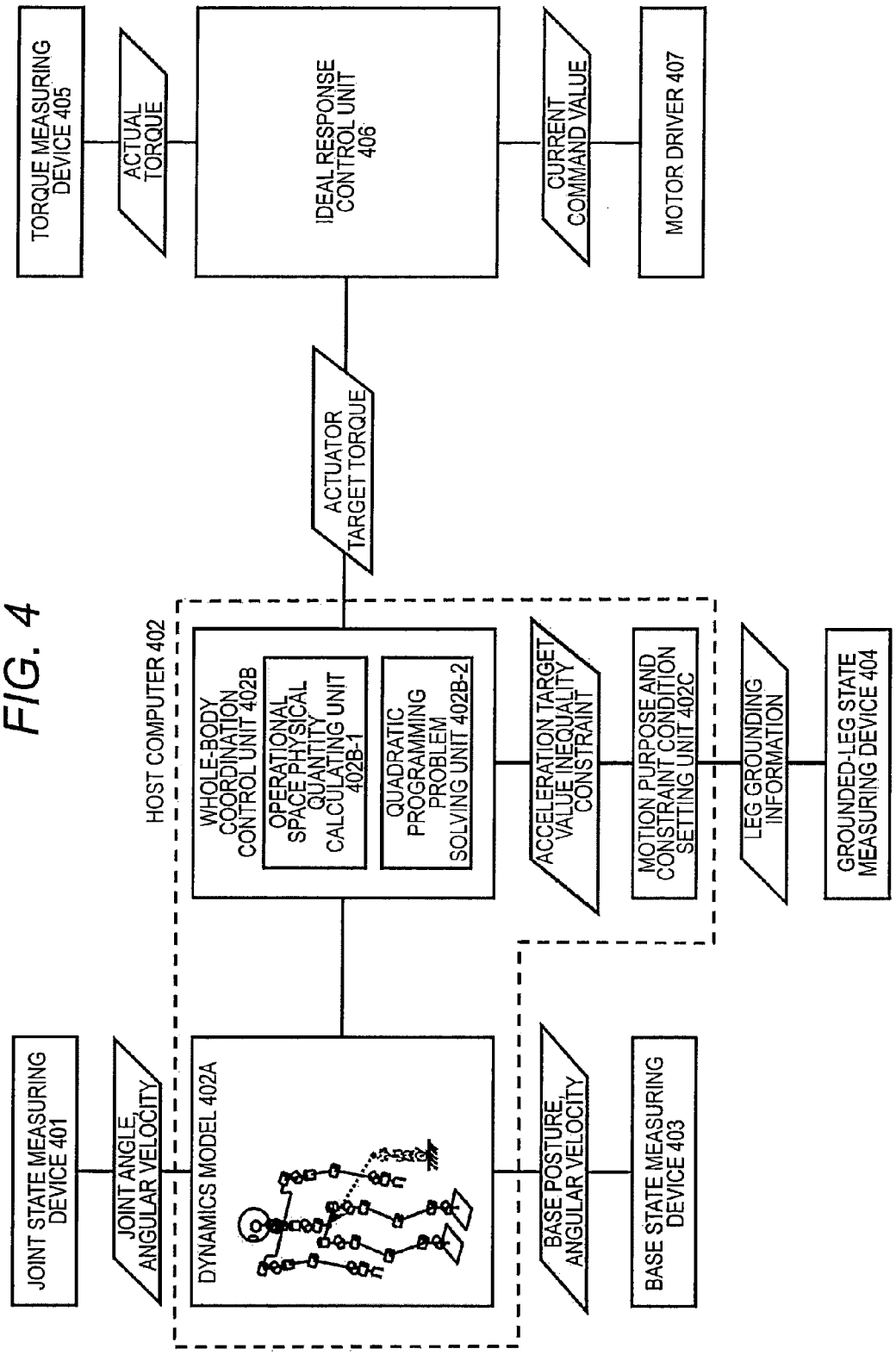
FIG. 4 is a diagram showing the control system configuration of the leg assist suit shown in FIGS. 1 to 3.

FIG. 4 shows the control system configuration of the leg assist suit shown in FIGS. 1 to 3. The control system in the drawing is formed with a joint state measuring device 401, a host computer 402, a base state measuring device 403, a grounded-leg state measuring device 404, a torque measuring device 405, an ideal response control unit 406, and a motor driver 407. The host computer 402 includes a dynamics model 402A, a whole-body coordination control unit 402B, and a motion purpose and constraint condition setting unit 402C.

Specifically, the joint state measuring device 401 is equivalent to the encoders and the tacho generators attached to the actuators for actuating the respective joints, and measures angles and angular velocities of the joints. As described above, joint angular velocities are regarded as 0 on a practical level so as to prevent the assisting force of the leg assist suit from becoming hyperreactive. In that case, angular velocity measurement by the joint state measuring device 401 can be skipped.

The base state measuring device 403 calculates a posture and an angular velocity of the pelvic region by using a value detected by an inertia sensor (an acceleration sensor and a gyroscope) installed in the pelvic region of the leg assist suit. Since bearings are not particularly essential, the base state measuring device 403 is designed to detect only tilts of the two axes of roll and pitch indicating a posture. As described above, the angular velocity of the base is regarded as 0 on a practical level so as to prevent the assisting force of the leg assist suit from becoming hyperreactive. In that case, angular velocity measurement by the base state measuring device 403 can be skipped.

The joint angles $q_A$ and the angular velocities thereof obtained by the joint state measuring device 401, and the base posture $q_U$ and the angular velocity thereof obtained by the base state measuring device 403 are reflected by the dynamics model 402A in the host computer 402. The dynamics model 402A regards only a tilt of the pelvic region as important for the position and posture in the world coordinate system, and the other state quantities (the position and bearing of the pelvic region) are ignored and regarded as 0 in the dynamics model 402A.

The grounded-leg state measuring device 404 is equivalent to the grounding measurement switch (described above) provided on the soles of the right and left feet. The grounded-leg state measuring device 404 is on when the soles of the feet are in contact with the road surface, and is off when the soles of the feet at not in contact with the road surface.

The motion purpose and constraint condition setting unit 402C issues the acceleration zero command shown in the above equation (20) to all the actuated joints $q_A$, and sets the constraint condition shown in the above expression (15) with respect to the maximum joint force value in the control system. Also, the motion purpose and constraint condition setting unit 402O sets the translational acceleration and angular acceleration zero commands shown in the above equations (21) and (22) and the inequality constraint condition shown in the above expression (16) at the grounding point based on the leg grounding information obtained by the grounded-leg state measuring device 404.

The whole-body coordination control unit 402B determines target torques so as to cancel or reduce the load acting on the joints of the person due to gravity, using the leg assist suit and a dynamics model of the person who wears the leg assist suit. In this embodiment, the whole-body coordination control unit 402B includes an operational space physical quantity calculating unit 402B-1 and a quadratic programming problem solving unit 402B-2. The operational space physical quantity calculating unit 402B-1 calculates operational space physical quantities $\Lambda_H^{-1}$ and $c_H$ in accordance with the state of the system, using the above equations (18) and (19). Using the obtained operational space physical quantities, the quadratic programming problem solving unit 402B-2 then solves the quadratic programming problem shown in the above expressions (9) and (10), and calculates the actuated joint forces (target torques) $\tau_A$ that satisfy the motion purposes (see the above equations (20) to (22)) and the constraint conditions (see the above expressions (15) and (16)) set by the motion purpose and constraint condition setting unit 402O.

The actuated joint forces $\tau_A$ calculated by the whole-body coordination control unit 402B are given as torque command values for the actuators for actuating the respective joints to the ideal response control unit 406. In this embodiment, the actuator device disclosed in Japanese Patent Publication No. 4715863, which has already been assigned to the applicant, is used as each of the actuators for actuating the respective joints, for example.

The torque measuring device 405 is equivalent to the torque sensor that is attached to each of the actuators and measures external torque.

The ideal response control unit 406 performs precise joint acceleration control (torque control) on the actuated torques (target torques) t, calculated by the whole-body coordination control unit 403B and the external torque measured by the torque measuring device 405, so that the joints will give ideal quadratic responses.

The ideal response control unit 406 then calculates a current command value for the motor driver 407, and controls the current flowing in the motor so that the motor driver 407 will realize this current command value.

The leg assist suit according to this embodiment reads intentions of the user from motions of the joints of the user without the use of a myoelectric sensor, and accordingly, is easy to wear. However, it is necessary to eliminate the cause of hindrance to motions of the joints of the user, such as the viscous resistance of the gear portion in each joint unit. Even if the gear portion of a joint actuator has friction that is difficult to model, the ideal response control unit 406 compensates for the friction, and controls the joint units to follow an idealized mathematical model, so that idealized joint units (IJU) can be realized. As a result, a force to support motions can be generated without any resistance applied to the joints of the user wearing the leg assist suit.

In a dynamics calculation in a two-legged robot (see FIG. 3), an actuator is modeled according to the mathematical expression shown in the following equation (23).

$$I_a \ddot{q}_A = \tau_A - \tau_e - v_a \dot{q}_A \quad \text{[Mathematical Formula 23]}$$

In the above equation (23), $I_a$ represents a virtual inertia of the joint, $q_A$ represents the joint angle (obtained as an encoder output) of the joint, $\tau_A$ represents a target torque that is the command value of the generated torque of the joint, $\tau_e$ represents the external torque acting on the joint, and $v_a$ represents a virtual viscosity coefficient (unknown and difficult to model) in the joint.

As can be seen from the above equation (23), the theoretical model includes the external torque term $\tau_e$ acting on the joint. Therefore, to correct a response of the actuator in accordance with the theoretical model, it is necessary to detect the external torque $\tau_e$. In this embodiment, the torque sensor for measuring the external torque $\tau_e$ at the output axis of the decelerator is mounted on each actuator (see FIG. 2), and torque measurement results are collected by the microcomputer.

As each actuator gives a response in accordance with the theoretical model shown in the above equation (23), the joint angular acceleration of the left-hand side is invariably achieved when the right-hand side of the above equation (23) is determined. A disturbance observer that estimates a disturbance torque is used in constructing such a joint angular acceleration control system, so that a joint toque $\tau$ can be determined with high precision based on the theoretical response model.

Figure 7:
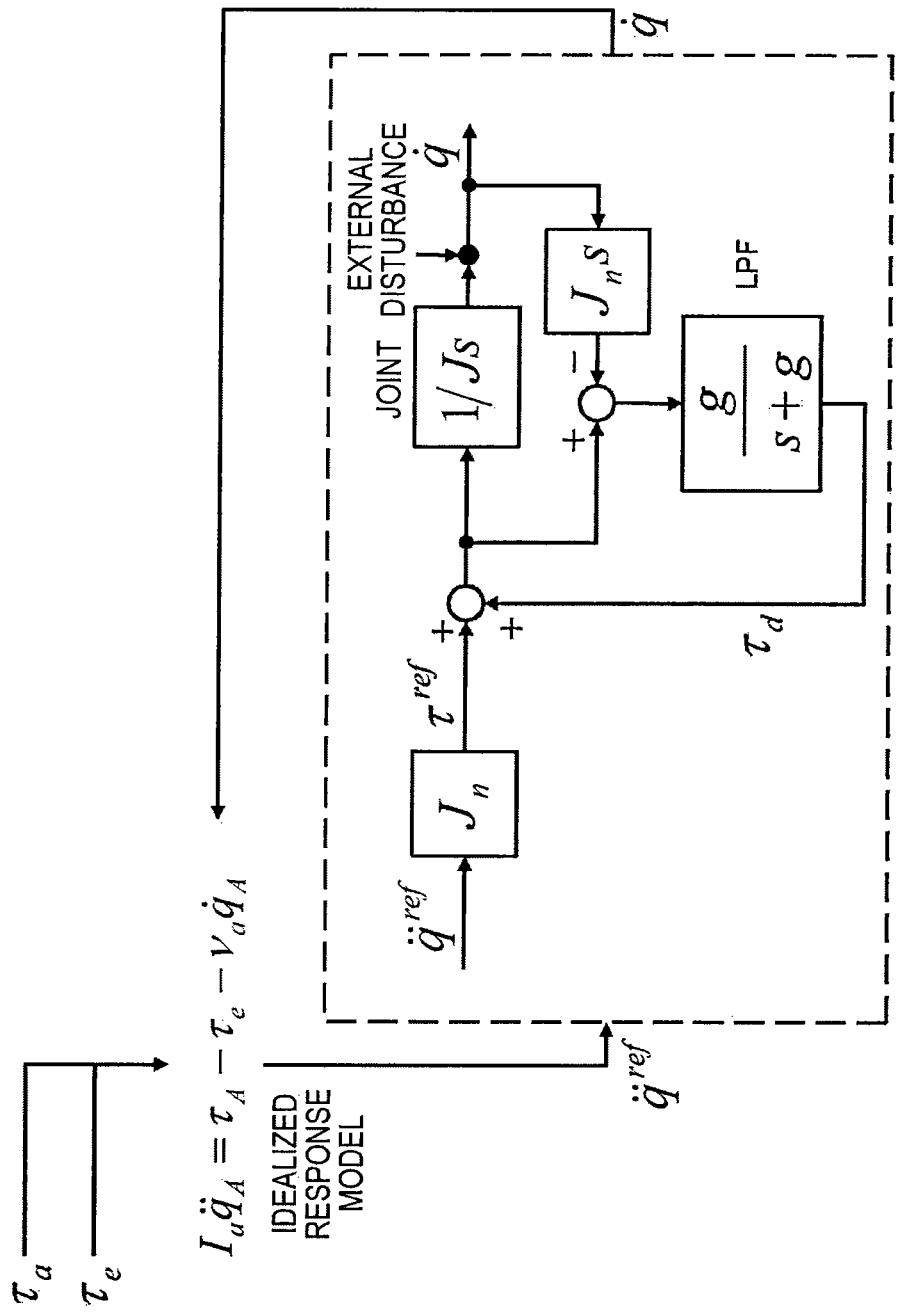
FIG. 7 is a control block diagram of the ideal response control unit 406.

FIG. 7 is a control block diagram of the ideal response control unit 406. In the drawing, the portion surrounded by the dashed line is equivalent to the disturbance observer that estimates a disturbance torque $\tau_d$ and eliminates influence on the control system, to form a robust acceleration control system. Here, $J_n$ represents the nominal value of the inertia in the joint, J represents the actual value (unknown) of the inertia in the joint, and $q_A$ represents the joint angle. Meanwhile, a virtual constant is assigned as a designing particular in a dynamics calculation to the virtual inertia $I_a$ of the joint.

In the host computer 402, in each control cycle, a target torque $\tau_A$ as a command value for the actuator is determined by a force control method, and an actual measured angular velocity value obtained from an actual external torque value $\tau_e$ measured by the torque measuring device 405 (the torque sensor attached to the output axis of the decelerator of the actuator) and a joint angle $q_A$ measured by the joint state measuring device 401 (the encoder attached to the rotator of the motor) is also sent from the microcomputer (described above) accompanying the actuator. The target torque $\tau_A$, the external torque $\tau_e$, and the actual measured angular velocity value of the joint angle $q_A$ are substituted into the theoretical response model shown in the above equation (1), to determine the acceleration target value of the joint angle $q_A$ in the left-hand side of the equation. This angular acceleration target value is input to the disturbance observer.

In the disturbance observer, the input acceleration target value of the joint angle $q_A$ is multiplied by the virtual inertia nominal value $J_n$, to be transformed into a torque target value $\tau^{ref}$ in the current control cycle. The torque target value $\tau^{ref}$ is then corrected with the disturbance torque $\tau_d$ obtained in the previous control cycle by the disturbance observer, to obtain a torque command value $\tau$ for the joint in the current control cycle.

When a joint formed with a transfer function $1/J_n$ is multiplied by force control formed with the torque command value $\tau$, the joint is rotationally actuated while being subjected to the influence of external disturbances such as friction and inertial existing in the joint unit. Specifically, the torque command value $\tau$ is converted into a current command value that is a command input for the motor driver 407. The generated torque $\tau_e$ and the joint angle $q_A$ at this point are measured by the torque measuring device 405 and the joint state measuring device 401, respectively, and the output $q_A$ of the joint state measuring device 401 is temporally differentiated, to obtain a joint angular velocity.

The disturbance observer can estimate the torque acting on the joint by applying a transfer function $J_n s$ formed with the virtual inertia nominal value $J_n$ of the joint to the angular velocity of the measured joint angle $q_A$, and this estimated torque is subtracted from the torque command value $\tau$, to estimate a disturbance torque $\tau_d$. The disturbance torque $\tau_d$ obtained in the current control cycle is fed back, and is used in correcting the torque command value $\tau$ in the next control cycle. A low-pass filter (LPF) that is inserted in the middle and is expressed as $g/(s+g)$ is a filter for preventing spreading of the system.

In the above manner, an acceleration response from an actuator can be made to follow an acceleration target value, even if there is a disturbance component such as friction or inertia that cannot be modeled in the joint unit. That is, as the joint angular acceleration in the left-hand side of the above equation (23) can be achieved when the right-hand side is determined, the actuator can realize a response in accordance with a theoretical model, despite being subjected to the influence of external disturbances. However, the above mentioned low-pass filter $g/(s+g)$ is inserted (as described above) while the disturbance torque $\tau_d$ is being fed back, and therefore, external disturbances in high-frequency regions are not efficiently removed.

As for the disturbance observer, please refer to "Robust Motion Control by Disturbance Observer" by Onishi (the Journal of the Robotics Society of Japan, Vol. 11, No. 4, pp. 486-493, 1993). The disturbance observer estimates an external disturbance component in the plant, and feeds back the estimate to a control input. Accordingly, the disturbance observer has the effect to achieve a target state even when there is an unknown parameter variation or an external disturbance in the plant. However, to estimate external disturbances correctly, it is necessary to repeat a feedback operation in cycles.

In the control block configuration shown in FIG. 7, the disturbance observer determines the angular acceleration of a joint angle q according to the above equation (23), and sets the angular acceleration to the joint angular acceleration target value for the actuator of the joint unit. The angular acceleration of the joint angle q is determined based on the external torque $\tau_e$ obtained from the torque measuring device 405, the target torque $\tau_A$ of the joint, and temporal differentiation of the joint angle $q_A$ output from the joint state measuring device 401 attached to the output axis of the decelerator. With this structure, the joint unit can make a response in accordance with the inertia $I_a$ and the viscosity coefficient $v_a$, and the response is idealized.

Figure 5:
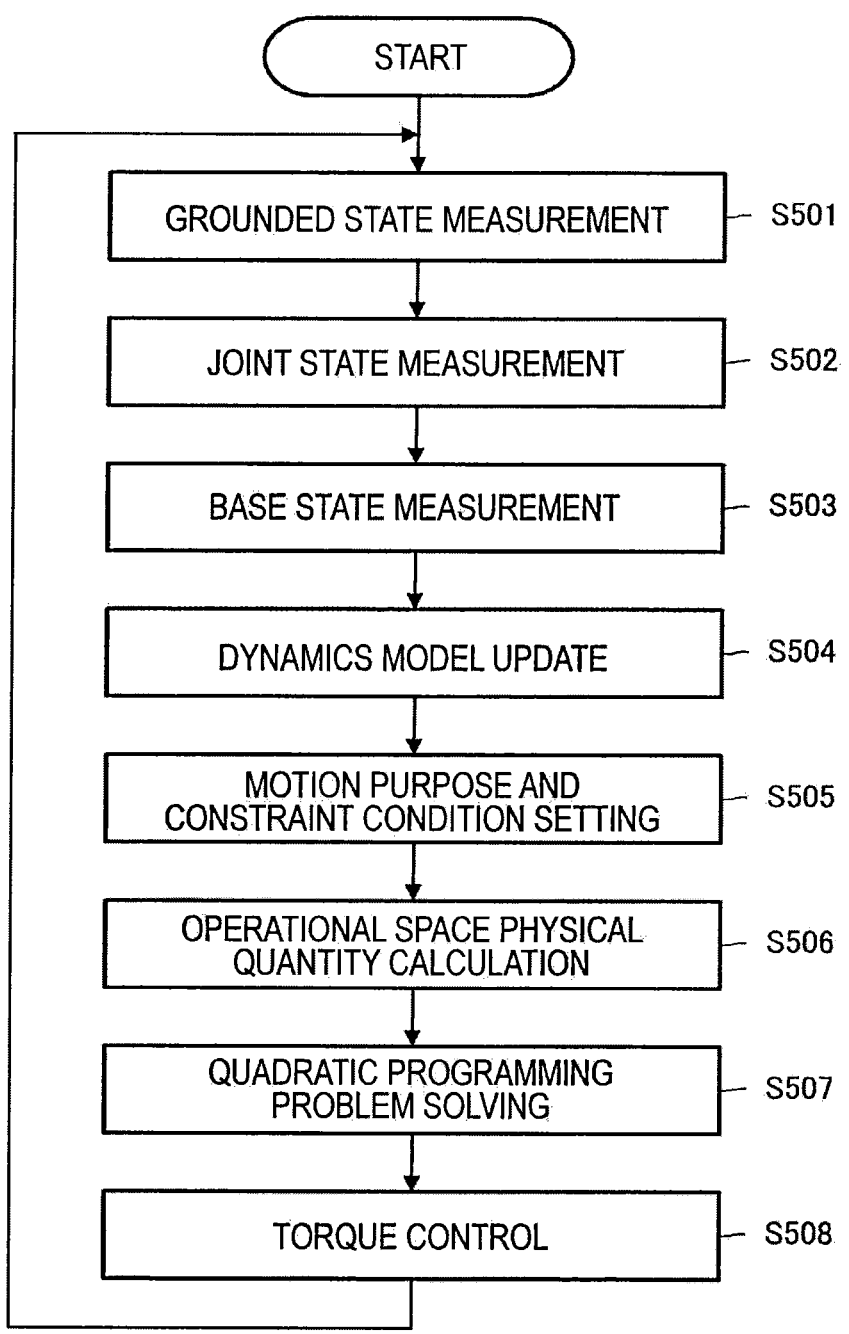
FIG. 5 is a flowchart showing the processing procedures to be carried out by the control system shown in FIG. 4.

FIG. 5 is a flowchart showing the processing procedures to be carried out by the control system shown in FIG. 4.

The grounded-leg state measuring device 404 measures an ON/OFF state of the grounding measurement switch attached to each of the soles of the right and left feet (step S501).

The joint state measuring device 401 counts the output values of the encoders attached to the actuators for actuating the respective joints, and obtains the current joint angle $q_A$ (step S502).

The base state measuring device 403 performs a posture calculation by reading the value detected by the inertia sensor (an acceleration sensor and a gyroscope) installed in the pelvic region of the leg assist suit, and obtains the posture of the pelvic region or the base (step S503).

The dynamics model 402A in the host computer 402 is then made to reflect the joint angle $q_A$ (as well as the angular velocity in some case) obtained by the joint state measuring device 401, and the base posture $q_U$ (as well as the angular velocity in some case) obtained by the base state measuring device 403 (step S504).

The motion purpose and constraint condition setting unit 402C then sets motion purposes and constraint conditions of the leg assist suit (step S505). Specifically, the motion purpose and constraint condition setting unit 402C issues the acceleration zero command shown in the above equation (20) to all the actuated joints $q_A$, and sets the constraint condition shown in the above expression (15) with respect to the maximum joint force value in the control system. Also, the motion purpose and constraint condition setting unit 402C sets the translational acceleration and angular acceleration zero commands shown in the above equations (21) and (22) and the inequality constraint condition shown in the above expression (16) at the grounding point based on the leg grounding information obtained by the grounded-leg state measuring device 404.

In the whole-body coordination control unit 402B, the operational space physical quantity calculating unit 402B-1 calculates operational space physical quantities $\Lambda_H^{-1}$ and $C_H$ in accordance with the state of the system, using the above equations (18) and (19) (step S506).

Using the operational space physical quantities obtained in step S506, the quadratic programming problem solving unit 402B-2 in the whole-body coordination control unit 402B then solves the quadratic programming problem shown in the above expressions (9) and (10), and calculates the actuated joint forces or the target torques $\tau_A$ that satisfy the motion purposes (see the above equations (20) to (22)) and the constraint conditions (see the above expressions (15) and (16)) set by the motion purpose and constraint condition setting unit 402C (step S507).

The whole-body coordination control unit 402B transmits the obtained target torques $\tau_A$ of the actuated joints $q_A$ to the ideal response control unit 406. The ideal response control unit 406 then performs precise joint acceleration control (torque control) on the actuated torques (target torques) $\tau_A$ calculated by the whole-body coordination control unit 403B and the external torque measured by the torque measuring device 405 as described above, so that the joints will give ideal quadratic responses (step S508).

The control system carries out the processing procedures shown in FIG. 5 at a control frequency of approximately 1 kHz, for example.

Figure 6:
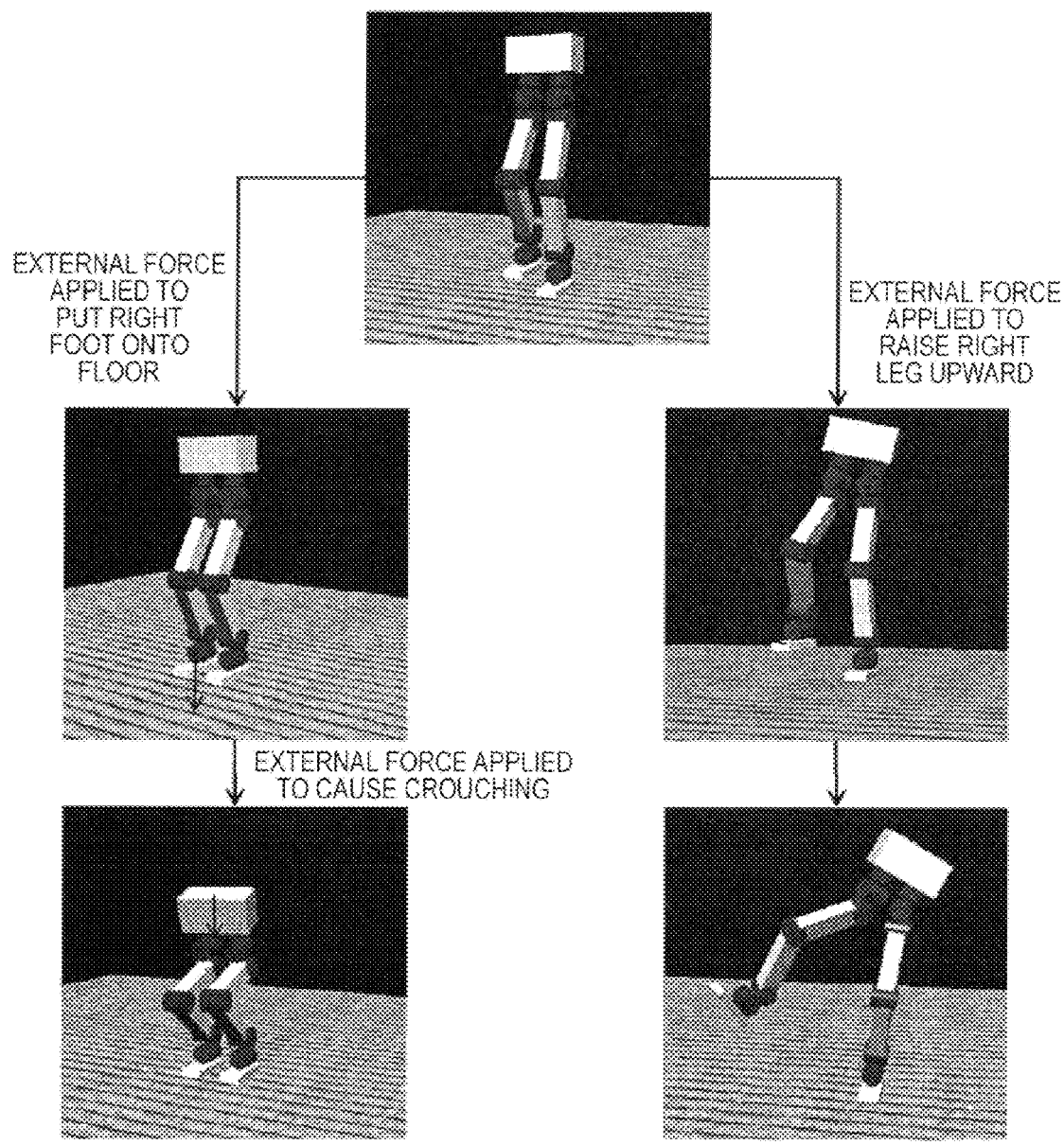
FIG. 6 is a diagram showing the results of experiments in which the control system realized by the control system shown in FIG. 4 was used in the two-legged robot model shown in FIG. 3.

FIG. 6 shows the results of experiments in which the control system realized by the control system shown in FIG. 4 was used in the two-legged robot model shown in FIG. 3.

In the postural change shown in the left column in FIG. 6 from a state where a person is standing on the left leg, an external force (a muscle force of the person wearing the suit) is applied to the right toe so that the right foot comes in contact with the floor. The posture passively changes to a two-leg supporting state. When the person is made to stand still in the two-leg supporting state, the motor maintains the joint acceleration at 0, and the same posture can be maintained without an external force (a muscle force of the person wearing the suit). Successively, an external force (a muscle force of the person wearing the suit) to crouch is applied to the pelvic region. The posture again passively changes, and the crouching position is kept. The motor then generates a joint force for maintaining the posture, and the same posture can be maintained without application of an external force (a muscle force of the person wearing the suit).

In the posture change shown in the right column in FIG. 6 from the state where the person is standing on the left leg, an external force (a muscle force of the person wearing the suit) is applied to the right toe, to raise the toe upward. The posture passively changes. After that, the person is made to stand still, and the external force (the muscle force of the person wearing the suit) is removed. The posture with the raised leg can also be maintained only with the force of the motor.

As described above, with the control system shown in FIG. 4, a posture passively changes in accordance with an external force (a muscle force of the person wearing the suit), and the joint force to maintain the posture can be generated by the motor in accordance with a grounded state. In this manner, the leg assist suit can assist the person wearing it to move as he/she wishes, without the use of the muscles of the person wearing it.

Although example cases where 100% of calculated forces are generated from the motor are shown in FIG. 6, assisting can be performed by generating a certain proportion (hereinafter referred to as the "assist ratio α") of a calculated torque from the force of the motor, and leaving some load applied to the muscles of the person wearing the suit. That is, a torque $\alpha \tau$ may be generated at actuated joints. The assist ratio can be determined in accordance with the degree of weakening of the physical capabilities of the person wearing the leg assist suit.

Also, in the above described embodiment, actuators are attached to all the joints of the legs of the person to be assisted (see FIG. 3). However, with a system having actuators attached to only some of the joints, leg movement of the person can be assisted by performing the same arithmetic operations as above. In the case where only some of the joints are assisted, however, dynamic consistency is not guaranteed, and therefore, no external force constraints are preferably imposed on contact points. Specifically, inequality constraints shown in the following expression (24), instead of the above expression (16), are imposed as contact constraints.

$$|F_x| \leq \infty, |F_y| \leq \infty, F_z \leq \infty$$

$$|M_x| \leq \infty, |M_y| \leq \infty, |M_z| \leq \infty \qquad \text{[Mathematical Formula 24]}$$

As described above, the lea assist suit according to this embodiment can read intentions of the user from movements of the joints of the user without a myoelectric sensor, and generate the force to support walking movements of the user. Since the assist suit does not use a myoelectric sensor, it is easy to wear the assist suit, and there is no risk of the myoelectric sensor running out of control even when the myoelectric sensor is detached from the skin while the user is moving. Also, the assist suit can smoothly provide a supporting force while following the user's movement as intended, without causing the user to feel uncomfortable due to friction at the joint units. The rule of force generation is not ad hoc but is based on the theory that the load on the joints of a person due to gravity is to be cancelled or reduced. Accordingly, the rule of force generation is not limited to particular motions, and a natural supporting force is constantly generated. Furthermore, there is no need to prepare control systems in accordance with grounded states of legs. Instead, it is possible to cope with various contact states of the whole body simply by increasing the number of installation sites of contact sensors such as the grounding measuring sensor for the soles of feet. The leg assist suit has such excellent mountability.

The technique disclosed in this specification can also have the following structures.

(1) A motion assist device including: a link structure formed with joint units and links that connect the joint units; an actuator that actuates the joint units through torque control; a joint value measuring unit that measures a joint value of the joint units; a target torque determining unit that determines a target torque for the actuator based on the joint value measured by the joint value measuring unit; a torque measuring unit that measures an external torque acting on the joint units; and a response control unit that performs torque control on the actuator, to establish a desired relationship among the target torque, the joint value measured by the joint value measuring unit, and the external torque measured by the torque measuring unit.

(2) The motion assist device of (1), wherein the target torque determining unit determines the target torque to reduce the load on the joints of a human body having the link structure attached thereto.

(3) The motion assist device of (1), wherein the target torque determining unit determines the target torque to make the accelerations of the joint units zero.

(4) The motion assist device of (1), further including a posture measuring unit that measures the tilt of part of the link structure. The target torque determining unit determines the target torque by using a dynamics model of the link structure and a human body having the link structure attached thereto, the dynamics model reflecting the tilt measured by the posture measuring unit and the joint value measured by the joint value measuring unit.

(5) The motion assist device of (4), wherein the target torque determining unit determines the target torque to cancel or reduce the load on the joints of the human body having the link structure attached thereto.

(6) The motion assist device of (5), further including a contact measuring unit that measures the contact state at a contact site where the link structure is assumed to be in contact with the outside. The target torque determining unit determines the target torque based on the contact state at the contact site measured by the contact measuring unit.

(7) The motion assist device of (6), wherein the target torque determining unit determines the target torque by using quadratic programming, the target torque satisfying a purpose of motion of the link structure and a constraint condition imposed on the link structure.

(8) The motion assist device of (1), wherein the response control unit performs the torque control on the actuator, to cause the joint units to make an ideal quadratic response to the target torque and the external torque measured by the torque measuring unit.

(9) The motion assist device of (1), wherein the response control unit includes a disturbance observer that calculates a disturbance torque $\tau_d$ when the actuator is actuated with the target torque $\tau_A$, and the response control unit corrects a torque target value $\tau^{ref}$ with the disturbance torque $\tau_d$ obtained by the disturbance observer in the previous control cycle to determine a command torque $\tau_e$ for the actuator in the current control cycle, the torque target value $\tau^{ref}$ being obtained by multiplying a joint value acceleration target value by the nominal value $J_n$ of inertia in the joint units, the joint value acceleration target value being obtained from a theoretical response model that is output by determining the joint value acceleration target value to be achieved when the actuator responds based on the target torque $\tau_A$, the external torque $\tau_e$, and a joint value velocity obtained by temporally differentiating the joint value q.

(10) A motion assist method including: a joint value measuring step of measuring a joint value of a joint unit in a link structure formed with joint units and links that connect the joint units; a target torque determining step of determining a target torque for an actuator based on the joint value measured in the joint value measuring step, the actuator actuating the joint units; a torque measuring step of measuring an external torque acting on the joint units; and a response control step of performing torque control on the actuator, to establish a desired relationship among the target torque, the joint value measured in the joint value measuring step, and the external torque measured in the torque measuring step.

(11) A computer program written in a computer-readable format to cause a computer to carry out: a joint value acquiring step of acquiring a joint value of a joint unit in a link structure formed with joint units and links that connect the joint units; a target torque determining step of determining a target torque for an actuator based on the joint value measured in the joint value measuring step, the actuator actuating the joint units; a torque acquiring step of acquiring an external torque acting on the joint units; and a response control step of performing torque control on the actuator, to establish a desired relationship among the target torque, the joint value acquired in the joint value measuring step, and the external torque measured in the torque acquiring step.

(12) A program recording medium storing a computer program written in a computer-readable format to cause a computer to carry out: a joint value acquiring step of acquiring a joint value of a joint unit in a link structure formed with joint units and links that connect the joint units; a target torque determining step of determining a target torque for an actuator based on the joint value measured in the joint value measuring step, the actuator actuating the joint units; a torque acquiring step of acquiring an external torque acting on the joint units; and a response control step of performing torque control on the actuator, to establish a desired relationship among the target torque, the joint value acquired in the joint value measuring step, and the external torque measured in the torque acquiring step.

INDUSTRIAL APPLICABILITY

The technique disclosed in this specification has been described in detail with reference to specific embodiments. However, it is obvious that a person skilled in the art can make changes and modifications to those embodiments without departing from the scope of the technique disclosed in this specification.

In this specification, embodiments applied to a leg assist suit have been mainly described. However, the scope of the technique disclosed in this specification is not limited to those embodiments. Various motions of a person other than walking can be assisted by applying the technique disclosed in this specification to various types of assist suits that are to be attached to sites of the person other than the legs.

In short, the technique disclosed in this specification has been described by way of examples, and the contents of this specification should not be interpreted in a restrictive manner. To determine the scope of the technique disclosed in this specification, the claims should be taken into account.

REFERENCE SIGNS LIST

401: Joint state measuring device
402: Host computer
402A: Dynamics model
402B: Whole-body coordination control unit
402C: Motion purpose and constraint condition setting unit
403: Base state measuring device
404: Grounded-leg state measuring device
405: Torque measuring device
406: Ideal response control unit
407: Motor driver

The invention claimed is:

1. A device comprising:
a link structure formed with a plurality of joints and a plurality of links connecting the joints;
an actuator that actuates the joints through torque control;
a joint value measuring device configured to measure a joint value of the joints;
a torque measuring device configured to measure an external torque acting on the joints; and
circuitry configured to
determine an actuator torque for the actuator based on the joint value measured by the joint value measuring device, and
perform torque control on the actuator based on the actuator torque, the joint value measured by the joint value measuring device, and the external torque measured by the torque measuring device,
wherein the circuitry is configured to determine a command torque for the actuator by correcting a torque target value with a disturbance torque when the actuator is actuated with the actuator torque, the torque target value being derived from a joint value acceleration target value that is based on the actuator torque, the joint value, and the external torque.

2. The device according to claim 1, wherein the circuitry is further configured to determine the actuator torque that reduces load on joints of a human body having the link structure attached thereto.

3. The device according to claim 1, wherein the circuitry is further configured to determine the actuator torque that makes acceleration of the joints zero.

4. The device according to claim 1, further comprising a posture measuring device configured to measure a tilt of part of the link structure,
wherein the circuitry is further configured to determine the actuator torque by using a dynamics model of the link structure and a human body having the link structure attached thereto, the dynamics model reflecting the tilt measured by the posture measuring device and the joint value measured by the joint value measuring device.

5. The device according to claim 4, wherein the circuitry is further configured to determine the actuator torque that cancels or reduces load on joints of the human body having the link structure attached thereto.

6. The device according to claim 5, further comprising a contact measuring device configured to measure a contact state at a contact site where the link structure is assumed to be in contact with an outside surface,
wherein the circuitry is further configured to determine the actuator torque based on the contact state at the contact site measured by the contact measuring device.

7. The device according to claim 6, wherein the circuitry is further configured to determine the actuator torque by using quadratic programming, the actuator torque satisfying a purpose of motion of the link structure and a constraint condition imposed on the link structure.

8. The device according to claim 1, wherein the circuitry is further configured to perform the torque control on the actuator, to cause the joints to make an ideal quadratic response to the actuator torque and the external torque measured by the torque measuring device.

9. The device according to claim 1, wherein the circuitry is further configured to
calculate the disturbance torque $\tau_d$ when the actuator is actuated with the actuator torque $\tau_A$, and
corrects the torque target value $\tau^{ref}$ with the disturbance torque $\tau_d$ obtained by a disturbance observer in a previous control cycle to determine the command torque $\tau_e$ for the actuator in a current control cycle, the torque target value $\tau^{ref}$ being obtained by multiplying the joint value acceleration target value by a nominal value $J_n$ of inertia in the joints, the joint value acceleration target value being obtained from a theoretical response model that is output by determining the joint value acceleration target value to be achieved when the actuator responds based on the torque $\tau_A$, the external torque $\tau_e$, and a joint value velocity obtained by temporally differentiating the joint value q.

10. A method comprising:
measuring a joint value of joints in a link structure formed with a plurality of joints and a plurality of links connecting the joints;
measuring an external torque acting on the joints;
determining an actuator torque for an actuator based on the measured joint value;
performing torque control on the actuator based on the actuator torque, the measured joint value, and the measured external torque; and
determining a command torque for the actuator by correcting a torque target value with a disturbance torque when the actuator is actuated with the actuator torque, the torque target value being derived from a joint value acceleration target value that is based on the actuator torque, the joint value, and the external torque.

11. A non-transitory computer readable medium having stored thereon a program written in a computer-readable format that when executed by a computer causes the computer to carry out a method comprising:
acquiring a joint value of joints in a link structure formed with a plurality of joints and a plurality of links connecting the joints;
acquiring an external torque acting on the joints;
determining an actuator torque for an actuator based on the measured joint value;
performing torque control on the actuator based on the actuator torque, the acquired joint value, and the acquired external torque; and
determining a command torque for the actuator by correcting a torque target value with a disturbance torque when the actuator is actuated with the actuator torque, the torque target value being derived from a joint value acceleration target value that is based on the actuator torque, the joint value, and the external torque.

12. A non-transitory computer readable medium having stored thereon a program written in a computer-readable format that when executed by a computer causes the computer to carry out a method comprising:
- measuring a joint value of joints in a link structure formed with a plurality of joints and a plurality of links connecting the joints;
- measuring an external torque acting on the joints;
- determining an actuator torque for an actuator based on the measured joint value;
- performing torque control on the actuator based on the actuator torque, the measured joint value, and the measured external torque; and
- determining a command torque for the actuator by correcting a torque target value with a disturbance torque when the actuator is actuated with the actuator torque, the torque target value being derived from a joint value acceleration target value that is based on the actuator torque, the joint value, and the external torque.

* * * * *